United States Patent [19]

Lubowitz et al.

[11] Patent Number: 5,756,645
[45] Date of Patent: May 26, 1998

[54] MULTIDIMENSIONAL POLYESTERS

[75] Inventors: Hyman R. Lubowitz, Rolling Hills Estates, Calif.; Clyde H. Sheppard, Bellevue, Wash.; Ronald R. Stephenson, Kirkland, Wash.

[73] Assignee: The Boeing Company, Seatte, Wash.

[21] Appl. No.: 470,370

[22] Filed: Jun. 6, 1995

Related U.S. Application Data

[60] Continuation of Ser. No. 161,164, Dec. 3, 1993, abandoned, which is a division of Ser. No. 176,518, Apr. 1, 1988, which is a continuation-in-part of Ser. No. 810,817, Dec. 17, 1985, abandoned, which is a continuation-in-part of Ser. No. 726,258, Apr. 23, 1985, abandoned.

[51] Int. Cl.$^6$ .................................................. C08G 63/82
[52] U.S. Cl. ........................ 528/282; 528/271; 528/272; 528/274; 528/282; 528/289; 528/292; 528/293; 528/295; 528/298; 528/299; 528/300; 524/175
[58] Field of Search ........................... 528/271, 274, 528/272, 282, 289, 292, 293, 295, 298, 299, 300; 524/175

[56] References Cited

U.S. PATENT DOCUMENTS

| | | | |
|---|---|---|---|
| 3,957,732 | 5/1976 | Hirooka et al. | 526/90 |
| 4,409,382 | 10/1983 | Keller | 528/173 |
| 4,542,203 | 9/1985 | Ueno et al. | |
| 4,547,553 | 10/1985 | Lubowitz et al. | 525/384 |
| 4,574,152 | 3/1986 | Noble | 544/4 |
| 4,617,390 | 10/1986 | Hoppe et al. | 544/197 |
| 4,709,008 | 11/1987 | Shimp | 528/422 |
| 5,210,213 | 5/1993 | Sheppard et al. | 548/435 |

OTHER PUBLICATIONS

Vinogradova et al., Chem. Abs. 67:100458, Vysokomal. Soedin., Ser. A (1967) 9(8) 1797–1801.
Vinogradova et al., Vysokomal. Soedin., Ser. A (1967) 9(8) 1797–1801.

*Primary Examiner*—Samuel A. Acquah
*Attorney, Agent, or Firm*—John C. Hammar

[57] ABSTRACT

The yield of fully substituted, multidimensional aromatic hubs in the condensation of hydroxyl and acid halide functionalities is improved by adding a thallium catalyst, such as thallium ethoxide (Tl-OC$_2$H$_5$), in the solvent.

14 Claims, No Drawings

MULTIDIMENSIONAL POLYESTERS

REFERENCE TO RELATED APPLICATION

The present application is a continuation of U.S. patent application Ser. No. 08/161,164, filed Dec. 3, 1993, now abandoned which is a Division of application Ser. No. 07/176,518 filed Apr. 1, 1988 which is a continuation-in-part application based upon U.S. patent application Ser. No. 810,817, filed Dec. 17, 1985, now abandoned which was a continuation-in-part application based upon U.S. patent application Ser. No. 726,258, filed Apr. 23, 1985, now abandoned.

TECHNICAL FIELD

The present invention relates to a method for making multidimensional polyesters using thallium ethoxide as a catalyst.

BACKGROUND OF THE INVENTION

In our earlier applications we proposed the condensation of hydroxyl (—OH) and carboxylic acid (—COOH) or carboxylic acid halides (—COX) on an aromatic hub having at least three such functionalities. The condensation occurred in a suitable solvent, such as DMAC, under an inert atmosphere in the presence of triethylamine (TEA). We have found that, when reacting, for example, phloroglucinol with an acid chloride end cap of the formula:

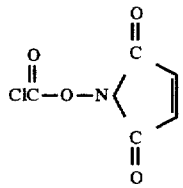

in DMAC and TEA that the resulting product is a mixture of

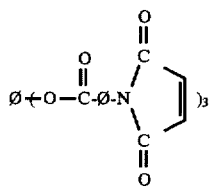   (I)

and

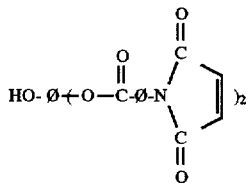   (II)

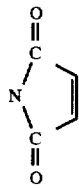

The condensation is difficult to drive to completion (i.e., replacement of all the —OH groups) to yield the desired product (I). The yield of fully reacted multidimensional ester (I) can be improved, however, by replacing the TEA with thallium ethoxide (Tl—OC$_2$H$_5$).

BEST MODE CONTEMPLATED FOR THE PRESENT INVENTION

The yield of multidimensional polyesters can be improved by replacing triethylamine (TEA) in the condensation solution with thallium ethoxide (Tl—OC$_2$H$_5$) as a catalyst. Since the polyester oligomers that are synthesized are often used without isolation of products, we believe that the new product, richer in product (I) [i.e. the truly multidimensional ester) will yield better composites than are achieved with the multidimensional (I) and linear (II) blend made using TEA as a catalyst.

The method of the present invention is equally applicable to use of an acid halide hub such as cyuranic acid chloride with a mono- or difunctional imidophenol end cap monomer. Chain-extension can be achieved, also, by including dialcohols, diacid halides, or both in the condensation mixture.

We believe that Tl—OC$_2$H$_5$ will produce a higher yield of the tri-substituted hub. If the hub has more than three reactive hydroxyl or acid halide functionalities, the thallium ethoxide catalyst will promote more complete reaction (or substitution) than TEA.

While thallium ethoxide is preferred, it is possible that any lower alkoxy substituent on the metal will be active as a catalyst. That is, methoxy, propoxy, isopropoxy, n-butoxy, phenoxy, or the like may also display catalytic activity.

Accordingly, the present invention relates to the catalysis of the —OH/—COX or —OH/—COOH condensation with a thallium catalyst, and, particularly, to the preparation of multidimensional polyesters by the condensation of Ar—(Q)$_w$ with a corresponding alcohol (—OH), acid (—COOH), or acid halide (—COX) in a suitable solvent under an inert atmosphere with or without heating in the presence of thallium ethoxide, wherein Ar=an aromatic radical of valency w;

w=an integer greater than or equal to 3; and

Q=—OH, —COOH, or —COX.

The aromatic radical will generally be phenyl or azalinyl, being the residue, for example of phloroglucinol or cyanuric acid. Those compounds described in U.S. Pat. Nos. 4,617,390 or 4,709,008 may also be used as hubs, and amine compounds can be reacted with an acid anhydride to form polycarboxylic acids that are suitable hubs. Triaminobenzene or the polyamines of U.S. Pat. No. 4,574,152 are suitable reactants (precursors) in this context.

The simplest oligomers can be prepared by condensing about 1 mole of the hub with a crosslinking end cap monomer of the formula:

D$_i$–θ–P wherein θ=phenol;

P=—COX, if the hub is a polyol, or —OH, if the hub is a polybasic acid;

i=1 or 2;

D=an unsaturated hydrocarbon radical that generally includes a segment selected from the group consisting of:

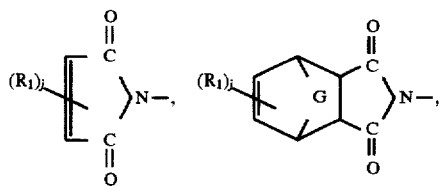

-continued

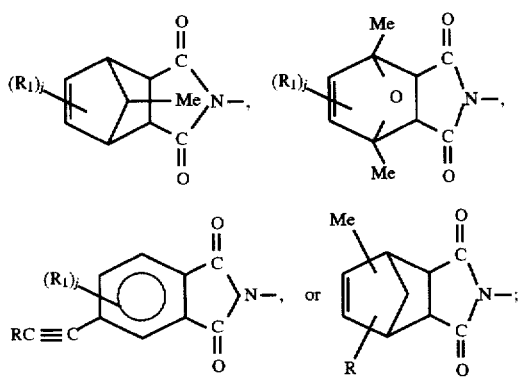

$R_1$=lower alkyl, aryl, substituted alkyl, substituted aryl, lower alkoxy, aryloxy, halogen, or mixtures thereof;
G=—O—, —S—, —SO$_2$—, —CH$_2$, —CO—, —CHR—, —SO—, or —CR$_2$—;
j=0, 1, or 2;
T=allyl or methallyl;
Me=methyl; and
R=hydrogen, lower alkyl, or phenyl.

These end cap monomers allow the multidimensional polyester oligomers to be cured into high performance, advanced composites that have use temperature that exceed (often substantially) their curing temperatures.

The arms of the multimdimensional oligomers can be extended if the reaction solution's components are adjusted. For example, the hub of the formula Ar—(Q)$_w$ can be simultaneously condensed with R—(P)$_2$ wherein
Ar=an aromatic radical of valency w;
w=a small integer greater than or equal to 3;
Q=—COX, —OH, or —COOH;
R=a divalent hydrocarbon radical, especially a phenoxyphenylsulfone; and
P=—OH, if Q=—COX or —COOH, or —COX or —COOH, if Q=—OH
with a crosslinking end cap monomer of the formula:

D$_i$-∅-Q wherein D, i, ∅, or Q are as previously defined.

The dialcohols or diacid halides include those compounds disclosed in U.S. Pat. No. 4,547,553 or in our copending applications.

The reaction solution may include four or more component mixtures but deleterious or interfering competitive reactions are likely to occur, dictating staged reaction rather than simultaneous condensation. For example, Ar—(Q)$_w$ can be condensed with R—(P)$_2$ followed by addition of R$_1$—(Q)$_2$ and D$_i$-∅-P to form a multidimensional polyester having extended arms (i.e., arms of relatively high average formula weight).

While preferred embodiments have been described, those skilled in the art will readily recognize alterations, variations, or modifications which might be made to the embodiments without departing from the inventive concept. Therefore, the claims should be interpreted liberally with the support of the full range of equivalents known to those of ordinary skill based upon this description. The claims should be limited only as is necessary in view of the pertinent prior art.

We claim:

1. A multidimensional polyester obtained by the process of simultaneously condensing in the presence of an effective amount of a thallium catalyst about 1 mole of a compound of the formula: Ar-(Q)$_w$ with about w moles of a compound of the formula: Φ-(P)$_2$ and about w moles of a compound of the formula: Ψ-Q wherein Ar is an aromatic radical of valency w;

w is a small integer greater than or equal to 3;

Q is —OH or —COX;

X is halogen;

Φ is a divalent hydrocarbon radical that is

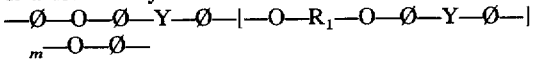

or is the residue of a dialcohol or a diacid halide selected from the group consisting of:
ethylene glycol;
1,2-butane diol;
1,3-butane diol;
1,4-butane diol;
1,6-hexane diol;
hydroquinone;
bisphenol -A;
4,4'-dihydroxydiphenylsulfide;
4,4'-dihydroxydiphenylsulfone;
4,4'-dihydroxydiphenylether; and
4,4'-dihydroxydiphenylhexafluoropropane;

Y is selected from the group consisting of sulfone, sulfoxide, sulfide, carbonyl, and perfluoroisopropenyl;

R$_1$ is selected from the group consisting of diphenyleneisopropane, phenylene, biphenylene, diphenylenesulfide, diphenylsulfone, diphenylene ether, and diphenylenehexafluoropropane;

m is an integer having a value of from 0–4;

P is —OH, if Q=—OH, or —COX, if Q=—OH;

Ψ is an organic radical selected from the group consisting of compounds of the formula:

i is 1 or 2;

∅ is phenylene;

D is an unsaturated hydrocarbon radical selected from the group consisting of:

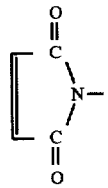

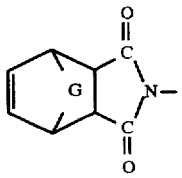

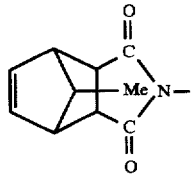

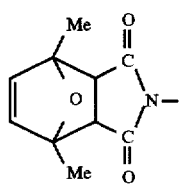

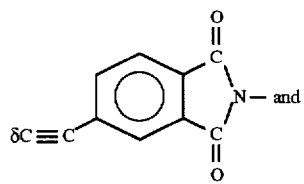

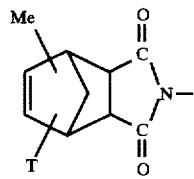

G=—O—, —S—, —SO$_2$—, —CH$_2$—, or —CO—;
T =allyl or methallyl;
Me=methyl; and
δ=hydrogen or phenylene.

2. A multidimensional polyester curable into a high performance, advanced composite that has a use temperature that exceeds its curing temperature of the formula.

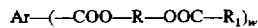

made by condensing about stoichiometric amounts of Ar-(Q)$_w$ with a diol containing R and an acid halide containing R$_1$ under an inert atmosphere in the presence of an effective amount of thallium catalyst to promote essentially complete substitution of the Ar radical,
wherein Ar is phenylene;

R is a residue of a diol selected from the group consisting of:
bisphenol-A,
4,4'-dihydroxydiphenylsulfide,
4,4'-dihydroxydiphenylsulfone,
4,4'-dihydroxydiphenylether, and
4,4'-dihydroxydiphenylhexafluoropropane;

R$_1$ is a monovalent, unsaturated organic radical selected from the group consisting of:

i is 1 or 2;
Ø is phenylene;
D is

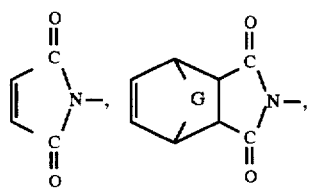

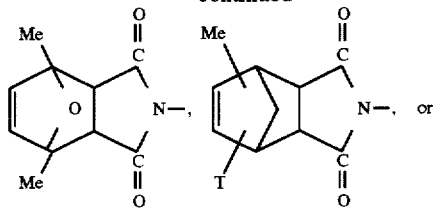

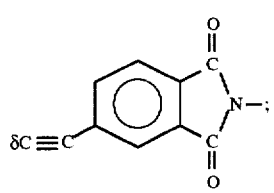

G is —O—, —S—, —CO—, CH$_2$—, —SO—, or —CH (Me)—;

δ is hydrogen or phenylene;

T is allyl or methallyl; and

Me is methyl.

3. A multidimensional polyester curable into high performance, advanced composite that has a use temperature that exceeds its curing temperature of the formula:

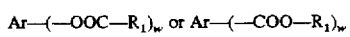

obtained by condensing substantially stoichiometric proportions of a compound of the formula:

with a compound of the formula R$_1$—P in the presence of an effective amount of a thallium catalyst to promote essentially complete substitution of the Ar radical;

wherein Ar is phenylene or a residue cyanuric acid;

w is a small integer greater than or equal to 3;

Q is —OH or —COX;

X is halogen;

P is —COX, if Q is —OH and
is —OH, if Q is —COX;

R$_1$ is a monovalent, unsaturated organic raidcal selected from the group consisting of:

Ø is phenylene;
i is 1 or 2;
D is

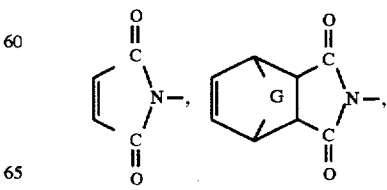

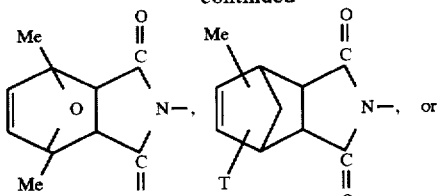

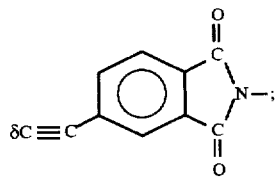

G is —O—, —S—, —CO—, CH$_2$—, —SO—, or —CH(Me)—;

δ is hydrogen or phenylene;

T is allyl or methallyl; and

Me is methyl.

4. A multidimensional polyester curable into a high performance, advanced composite that has a use temperature that exceeds its curing temperature of the formula:

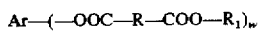

obtained by condensing about stoichiometric amounts of Ar—(OH)$_w$ with a diacid halide containing residue R and with R$_1$—OH under an inert atmosphere in the presence of a thallium catalyst to promote essentially complete substitution of the Ar radical, wherein Ar is phenylene or a residue of cyanuric acid;

R is residue selected from the group consisting of
—∅—,
—∅—S—∅—
—∅—SO$_2$—∅—
—∅—O—∅—, and
—∅—C(CF$_3$)$_2$—∅—;

R$_1$ is a monovalent, unsaturated organic radical selected from the group consisting of:

i is 1 or 2;

∅ is phenylene;

D is

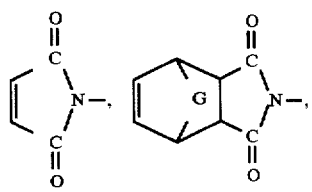

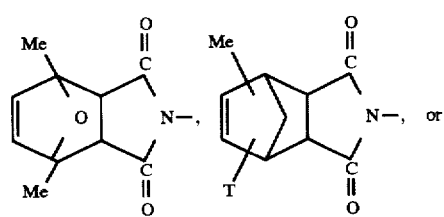

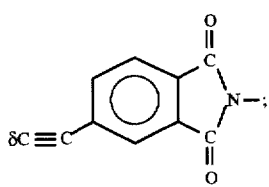

G is —O—, —S—, —CO—, CH$_2$—, —SO—, or —CH(Me)—;

δ is hydrogen or phenylene;

T is allyl or methallyl; and

Me is methyl.

5. The polyester of claim 2 wherein i is 2.

6. The polyester of claim 2 wherein D is

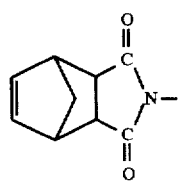

7. The polyester of claim 2 wherein D is

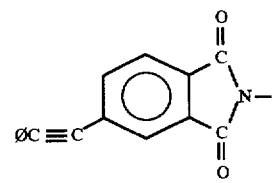

8. The polyester of claim 4 wherein D is

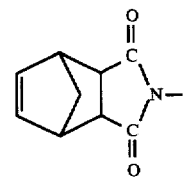

9. The polyester of claim 3 wherein D is

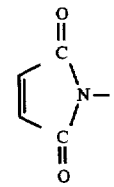

10. The polyester of claim 4 wherein D is
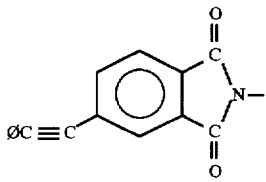
11. The polyester of claim 2 wherein D is
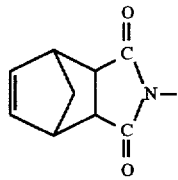
12. The polyester of claim 2 wherein D is
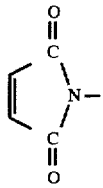
13. The polyester of claim 2 wherein D is
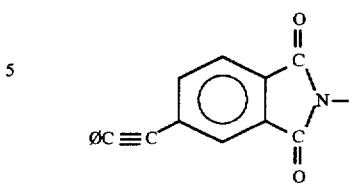
14. The polyester of claim 1 wherein D is selected from the group consisting of:
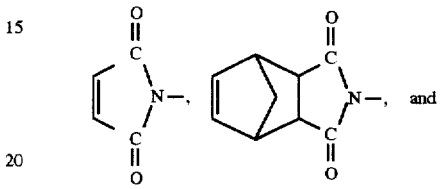
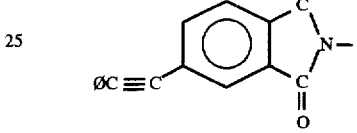
* * * * *